United States Patent [19]

Cimbollek et al.

[11] Patent Number: 5,607,685
[45] Date of Patent: Mar. 4, 1997

[54] PROTRACTED-RELEASE ADMINSTRATION FORMS CONTAINING CLINDAMYCIN PALMITATE

[75] Inventors: Monika Cimbollek, Mannheim; Berthold Nies, Fränkisch-Crumbach, both of Germany

[73] Assignee: Merck Patent Gesellschaft Mit Beschrankter Haftung, Darmstadt, Germany

[21] Appl. No.: 385,428

[22] Filed: Feb. 8, 1995

[30] Foreign Application Priority Data

Feb. 9, 1994 [DE] Germany .......................... 44 04 018.0

[51] Int. Cl.⁶ ................................... A61K 31/40
[52] U.S. Cl. ........................ 424/422; 424/423; 424/424; 424/435; 514/42; 514/43; 514/964
[58] Field of Search .................... 424/422, 423, 424/424, 435; 514/42, 93, 964; 536/16.4, 16.5, 17.5

[56] References Cited

U.S. PATENT DOCUMENTS 5,202,128  4/1993  Morella et al. .......................... 424/469
5,378,474  1/1995  Morella et al. .......................... 424/469

Primary Examiner—Nathan M. Nutter
Attorney, Agent, or Firm—Millen, White, Zelano, & Branigan, P.C.

[57] ABSTRACT

The invention relates to the use of clindamycin palmitate for the production of pharmaceutical administration forms having a protracted release of the antibiotic active compound clindamycin, and corresponding administration forms which are preferably used in the form of shaped implants.

9 Claims, 2 Drawing Sheets

PROTRACTED-RELEASE ADMINSTRATION FORMS CONTAINING CLINDAMYCIN PALMITATE

BACKGROUND OF THE INVENTION

The invention relates to the use of clindamycin palmitate for the production of pharmaceutical administration forms having a protracted release of the antibiotic active compound clindamycin and to corresponding administration forms, in particular in the form of shaped implants.

Clindamycin is an antibiotic of generally recognized value. It exhibits particular effectiveness against Gram-positive organisms such as staphylococci and streptococci and also against Gram-negative anaerobes. This antibiotic is therefore used for the treatment of a wide spectrum of diseases, e.g., in the control of infections of the digestive tract, the skin and the soft tissue and also in osteomyelitis and in gynecological infections. Clindamycin has furthermore been successfully employed in prophylaxis and therapy of bacterial endocarditis.

In the indications mentioned, this antibiotic is used in the form of physiologically acceptable salts such as, for example, clindamycin HCl, clindamycin phosphate ester or alternatively in the form of free clindamycin base.

Clindamycin is also known in the form of the palmitate ester. Clindamycin palmitate itself is microbiologically inactive. However, it is readily hydrolyzed by enzymes of the small intestine and the active clindamycin base is released from this form. The plasma half-life of the active compound is in this case about 2 hours. As a result of this property, clindamycin palmitate has found use in the form of the HCl salt, which is readily soluble in aqueous medium, as a rapid- and short-acting antibiotic in therapy forms where the active compound is administered orally. The free clindamycin palmitate ester (i.e., not in the form of the HCl salt) is virtually insoluble in aqueous media and therefore until now remained pharmacologically unimportant.

SUMMARY OF THE INVENTION

Surprisingly, it has now been found that the hydrolysis of clindamycin palmitate to the active clindamycin can take place not only in the gastrointestinal tract, but also in other sites of the body under the influence of body fluids such as serum and blood. By means of in vitro experiments, it was found that in serum or whole blood or under the influence of macrophages, the active clindamycin base was released slowly from clindamycin palmitate, over a period of days to weeks, at an approximately constant rate. As a result of these findings, the basic suitability of clindamycin palmitate per se emerges as a depot antibiotic to be employed locally, for example, on operation wounds, for the prophylaxis and therapy of infections, due to the protracted release of the active compound clindamycin.

Clindamycin palmitate is especially suitable for the production of pharmaceutical administration forms having a protracted release of the antibiotic active compound clindamycin.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION OF THE INVENTION

Figure 1:
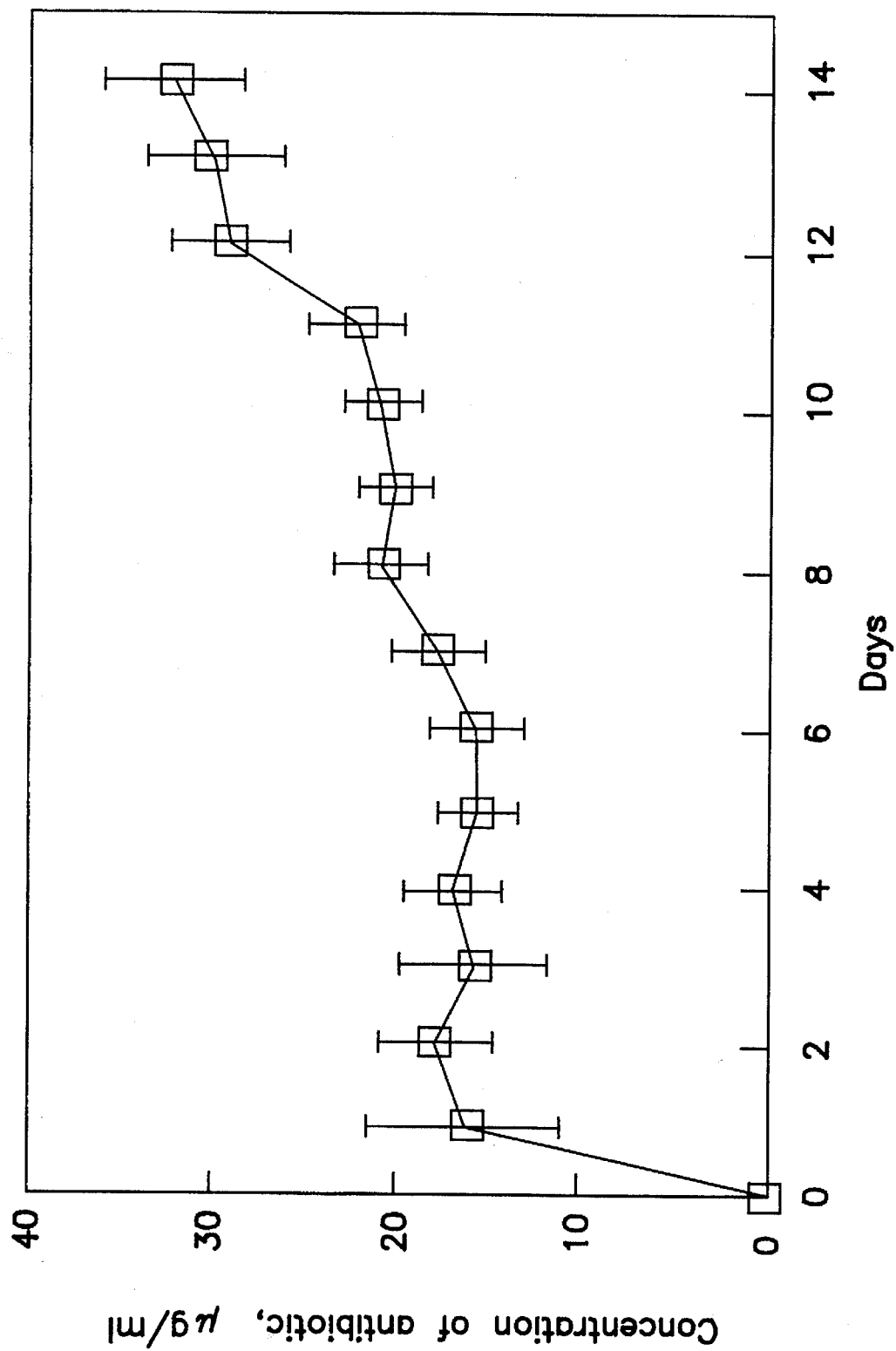
FIG. 1 shows the release of clindamycin from a Teflon nonwoven implanted in rat thigh as disclosed in Example 6.

The invention thus relates to the use of clindamycin palmitate for the production of pharmaceutical administration forms having a protracted release of the antibiotic active compound clindamycin.

The invention furthermore relates to pharmaceutical administration forms having a protracted release of the antibiotic active compound clindamycin, these containing clindamycin palmitate.

The invention in particular relates to pharmaceutical administration forms of this type in the form of shaped implants.

Upon further study of the specification and appended claims, further objects and advantages of this invention will become apparent to those skilled in the art.

The suitability according to the invention of clindamycin palmitate as a depot antibiotic for the production of administration forms having a protracted release of active compound results on the one hand from its low solubility in aqueous or physiological media and on the other hand from the hitherto undiscovered accessibility by metabolizing processes in body fluids, through which the active clindamycin base is released and can exhibit its antibiotic action. After an incubation time of 4 hours, hydrolysis of clindamycin palmitate to 70% and, after 24 hours, to 100% thus results, for example, from in vitro investigations in rat blood. In human serum and in horse serum, after this period 35% of the ester is cleaved to the active clindamycin base. In vivo experiments on rats which were implanted with pieces of clindamycin palmitate-impregnated nonwoven PTFE in the thigh muscle showed a constant to slightly increasing excretion of clindamycin base in the urine of the animals over a period of 14 days, while clindamycin palmitate could not be found. Additionally, clindamycin base could be detected in the muscle tissue surrounding the implant.

According to the invention, clindamycin palmitate can therefore be employed advantageously in pharmaceutical administration forms having a protracted release of the active compound clindamycin. Administration forms of this type are preferably produced in the form of shaped implants. These shaped implants are principally used in bone replacement in the treatment or reconstitution of bone defects caused by accident or disease. Furthermore, corresponding shaped implants can also be used for the replacement of other organ parts, such as, for example, as artificial cardiac valves, cardiac valve suture rings, artificial blood vessels or other surgical suture material. Shaped implants, however, can also be used only as depot implants for local release of active compound in the control or prophylaxis of infections.

The term "shaped implants" means that these implant materials have already obtained their final form or shape before they are loaded with the antibiotic. This refers, e.g., to porous bone substitutes, joint prostheses, vascular prostheses, etc. This is distinct from those methods of antibiotic loading which are done during the shaping or forming process of an implant material, e.g., bone cement. In the latter case, the release of the antibiotic is typically controlled by diffusion from a matrix and is highly dependent on the matrix properties. In contrast, in the present invention, the antibiotic release is not controlled by matrix properties but by the solution properties of the drug derivative itself.

Shaped implants of this type preferably contain 5 to 250 mg/cm$^3$ of clindamycin palmitate. In this concentration range, a release of active amounts of clindamycin lasting over a sufficient period is guaranteed for the customary indications.

In systemic (oral) therapy, clindamycin is applied in doses of 150–450 mg every 6 h or 3–25 mg/Kg every 6–8 h and maximum 1,800 mg/day. Intravenously, clindamycin is applied in maximum daily doses of 2,700 mg/day in 2–4 single doses. For children, the daily doses are generally in the range of 20–40 mg/kg.

In contrast, for local application as described in the invention, the amount of clindamycin is much lower, e.g., in case of heart valve sewing rings, approximately 100 mg or less, as one single dose. In the case of clindamycin-loaded bone substitutes, the amount of clindamycin is dependent on the volume of bone substitute which is implanted, typically less than 100 g. Even at a high loading of 50 mg/g, the total amount of clindamycin can be as little as 5 g, which is less than recommended for systemic therapy in two days, because the depot clindamycin is released slowly and, therefore, much less active drug is available to the body per time unit than in systemic therapy.

The combination of clindamycin palmitate with one or more further pharmaceutical active compounds is advantageous, in particular those likewise having an antibiotic action. In this case the spectrum of action can be widened and/or temporally and quantitatively different release rates of the different antibiotics combined.

Examples of further antibiotics of this type which can be combined with clindamycin palmitate are gentamicin sulfate and in particular the salt of gentamicin with 3-p-methoxy-benzylidene-6-hydroxy-4'-methoxy-flavanone-6-phosphate. The latter gentamicin salt is poorly soluble and therefore provides a depot form of gentamicin having a protracted release.

Suitable antibiotics to be combined with clindamycin are generally those which add to the antibacterial spectrum of this drug, especially aminoglycosides such as gentamicin, tobramycin, netilmicin and amikacin, and those beta-lactam antibiotics which have rather low activity themselves against staphylococci and/or anaerobic bacteria, such as the third generation cephalosporins, monobactams and members of other β-lactam antibiotic groups.

Further suitable partners can be routinely chosen from the different groups of antibiotics on the basis of the intended use of the clindamycin-loaded implant.

The use according to the invention of clindamycin palmitate for the production of pharmaceutical administration forms having a protracted release can be expediently carried out by impregnating a suitable carrier material, which is present in the form of a shaped implant or can be further processed to give one, with clindamycin palmitate such that its free outer and, if appropriate, inner surface and/or the matrix material itself is as uniformly loaded as possible with the active compound. Expediently, this impregnation is carried out using a liquid preparation of clindamycin palmitate which readily wets or penetrates the shaped implant. Such a liquid preparation can be a suspension or preferably a solution of the active compound.

It has been found that a mixture of 7 to 9 parts by volume of tetrahydrofuran and 3 to 1 parts by volume of water is a particularly good solvent for clindamycin palmitate. In tetrahydrofuran/water mixtures of this type, clindamycin can be dissolved to about 33% by weight. Solvent mixtures of this type are also particularly advantageous if clindamycin palmitate is to be employed in combination with the above-mentioned depot form of gentamicin. According to German Patent Application P 43 14 871, mixtures of this type are excellent solvents for this otherwise only poorly soluble gentamicin salt.

Suitable carrier materials for clindamycin palmitate, as well as other pharmaceutical active compounds are primarily porous materials which can readily absorb the active compound solution. Bioactive and in particular bioabsorbable materials are preferred which preferably are present in the form of shaped implants or can be processed to give these. Typical porous biomaterials for shaped implants are calcium phosphates such as, in particular, calcium phosphate ceramics. As a rule, these consist of hydroxyapatite of synthetic or natural origin. Bone ceramics are preferred which can be obtained from natural bone by removal of the organic part and sintering of the mineral phase to give the ceramic. Spongiosa ceramic is particularly suitable for impregnation with active compound on account of the naturally high porosity. Other calcium phosphate materials are tricalcium phosphate and tetracalcium phosphate, which are employed analogously.

Porous molded implants of bioinert polymer materials such as, for example, polytetrafluoroethylene ("Teflon") or of biopolymers such as collagen, gelatin, chitin, chitosan, polylactides or polyglycolides can likewise be impregnated with clindamycin palmitate in the manner according to the invention. Preferably, these materials are present in the form of absorbent structures having a spongy, nonwoven or woven fabric structure or as gels or waxy materials. Porous composite materials made from bioceramics and biopolymers are likewise suitable as active compound carriers.

The loading of the porous active compound carriers with clindamycin palmitate is expediently carried out by treating the carrier with the active compound solution by complete immersion or addition in the form of drops until the absorptive volume is completely filled with the solution. The carrier is then dried, preferably in a stream of warm air. Drying takes place relatively rapidly, as the tetrahydrofuran, which makes up the main part of the solvent mixture, evaporates rapidly. By means of this, the inner and outer surfaces of the shaped article receive a coating of the active compound which is uniform to the greatest possible extent. After sterilization, which is necessary in some cases, and sterile packaging, the shaped implants loaded with the active compound are ready for use.

By means of an analogous treatment with the clindamycin palmitate solution, non-porous or only rough-surface implants can also be coated with an active compound layer. An antibiotic coating having a protracted release of active compound of this type can be advantageous for many types of endoprostheses made from metal, ceramics or plastic. In addition to the high active compound concentration of the solution, this coating in this case additionally has the advantage that it readily wets and uniformly coats these materials. The antibiotic coating of the femur shaft of hip prostheses and the antibiotic impregnation of cardiac valve suture rings, for example, is advantageous.

In vitro and in vivo experiments with shaped implants which contain clindamycin palmitate show a long-lasting, uniform release of the antibiotically active clindamycin base, while release of the inactive clindamycin palmitate is not to be noted or to be noted only to a slight extent.

Without further elaboration, it is believed that one skilled in the art can, using the preceding description, utilize the present invention to its fullest extent, The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 44 04 018.0, are hereby incorporated by reference.

EXAMPLES

Example 1

Starting from a solution of 1 g of clindamycin palmitate HCl (Up-john, USA) in 25 ml of water, the clindamycin palmitate ester is precipitated by addition of 10 ml of a 0.1% normal NaOH solution, filtered off, washed with water and dried.

Example 2

0.1 g of the clindamycin palmitate ester according to Example 1 is suspended in 100 ml of a 1.5% liquid agar solution. After solidification, shaped articles of about 0.725 $cm^3$ are cut from the material.

These shaped articles are eluted in fresh, active human serum. The clindamycin activities in the eluates are microbiologically determined. The results show a zero-order release at a concentration of about 10 µg/ml for over more than 20 days.

Example 3

Clindamycin palmitate ester according to Example 1 is dissolved in a mixture of 9 parts by volume of THF and 1 part by volume of $H_2O$ with stirring at 25° C. to give a solution containing 0.33 g/ml.

Example 4

Blocks of porous hydroxyapatite ceramics of dimensions 12.5×12.5×10 mm prepared from natural spongiosa are impregnated by immersion using the solution according to Example 3. The ceramic blocks saturated with solution are removed and dried in a stream of warm air in the course of 2 hours. The ready-to-use blocks contain about 120 mg of clindamycin palmitate.

Example 5

Circular Teflon nonwovens of diameter 0.5 cm and thickness 0.2 cm are immersed in the solution according to Example 3 until they have become completely saturated. They are then removed and dried for about 30 minutes in a stream of warm air. The ready-to-use nonwovens contain 25 mg of clindamycin palmitate.

Example 6

Teflon nonwovens according to Example 5 are implanted in the thigh muscles of 6 rats. The animals are kept in metabolism cages. The release of antibiotic is determined daily in the collected urine in the course of a period of 2 weeks.

FIG. 1 shows the result.

Over the test period, no clindamycin palmitate, but a content of antibiotically active clindamycin slightly increasing from 16 to 32 µg/ml, was detected in the urine.

Example 7

Segments of cardiac valve suture rings (Sorin, Italy) are first impregnated with a solution of 9 parts by volume of THF and 1 part by volume of $H_2O$ containing 0.33 g/ml of clindamycin palmitate and 0.1 g/ml of the salt of gentamicin with 3-p-methoxybenzylidene-6-hydroxy-4'-methoxyflavanone-6-phosphate and dried. The segments are then immersed in an aqueous solution containing 0.03 g/ml of gentamicin sulfate and dried again. In this manner, suture ring segments are obtained which contain 20 mg of clindamycin palmitate, 14 mg of the poorly soluble gentamicin salt and 4 mg of gentamicin sulfate.

These segments are implanted in the thigh muscles of 5 rats. The animals are kept in metabolism cages. The release of antibiotic is determined daily in the collected urine in the course of a period of 2 weeks.

Figure 2:
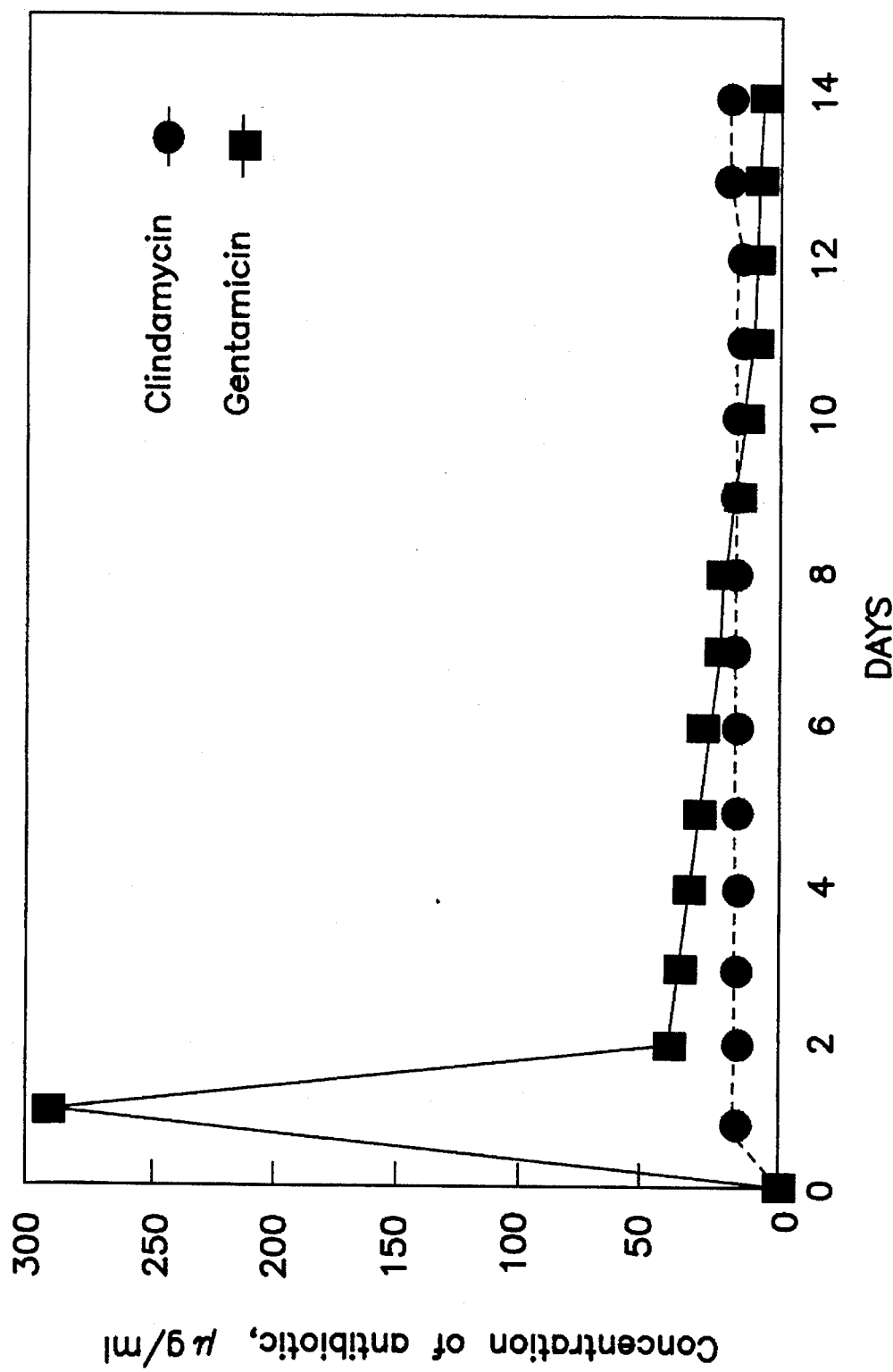
FIG. 2 shows the release of clindamycin and gentamicin from cardiac valve suture rings implanted in rat thigh as disclosed in Example 7.

FIG. 2 shows the result.

Over the test period, no clindamycin palmitate, but a constant content of about 14 µg/ml of clindamycin, was detected in the urine. The release curve for gentamicin shows an initial peak value of 290 µg/ml within the first 24 hours, which is followed by a protracted release falling from 38 to 3.5 µg/ml.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical preparation having a protracted release of the antibiotic active compound clindamycin in blood or serum in the form of a shaped implant, comprising an active compound carrier impregnated with clindamycin palmitate.

2. A pharmaceutical preparation of claim 1, wherein the shaped implant contains 5 to 25 mg/$cm^3$ of clindamycin palmitate.

3. A pharmaceutical preparation of claim 1, further comprising an additional pharmaceutically active compound.

4. A pharmaceutical preparation of claim 3, wherein the additional pharmaceutically active compound is an antibiotic.

5. A pharmaceutical preparation of claim 4, wherein the additional pharmaceutically active compound is gentamicin sulfate and/or the salt of gentamicin with 3-p-methoxybenzylidene-6-hydroxy-4'-methoxyflavanone-6-phosphate.

6. A pharmaceutical preparation of claim 1, wherein the active compound carrier comprises a bioinert or bioabsorbable polymer material having a spongy, nonwoven or woven fabric structure.

7. A pharmaceutical preparation of claim 1, wherein the active compound carrier comprises a porous ceramic material.

8. A pharmaceutical preparation of claim 7, wherein the porous ceramic material is based on calcium phosphate.

9. A process for the production of an implantable pharmaceutical preparation having a protracted release of clindamycin, comprising:

dissolving clindamycin palmitate and, optionally, an additional pharmaceutically active compound, in a mixture of 7–9 parts by volume of tetrahydrofuran and 3–1 parts by volume of water, treating an active compound carrier with this solution, and removing the solvent by drying.

\* \* \* \* \*